US008609040B2

(12) United States Patent
Brown et al.

(10) Patent No.: US 8,609,040 B2
(45) Date of Patent: Dec. 17, 2013

(54) SYSTEM FOR CREATION OF FORMULATIONS AND GENERATION OF DENATURATION GRAPHS

(75) Inventors: Richard Brown, East Falmouth, MA (US); Burleigh Hutchins, West Brookfield, MA (US); Ernesto Freire, Baltimore, MD (US)

(73) Assignee: AVIA Biosystems, LLC, East Falmouth, MA (US)

( * ) Notice: Subject to any disclaimer, the term of this patent is extended or adjusted under 35 U.S.C. 154(b) by 0 days.

(21) Appl. No.: 13/214,361

(22) Filed: Aug. 22, 2011

(65) Prior Publication Data

US 2012/0045367 A1 Feb. 23, 2012

Related U.S. Application Data

(60) Provisional application No. 61/375,920, filed on Aug. 23, 2010.

(51) Int. Cl.
*B01L 3/02* (2006.01)
(52) U.S. Cl.
USPC ........... 422/509; 422/501; 422/518; 422/521; 422/63; 422/67; 422/68.1; 73/863.32; 73/864; 73/864.01; 73/864.11; 73/864.24; 73/864.25
(58) Field of Classification Search
USPC .......... 422/63–68.1, 501, 509, 516, 518, 521; 73/863.32, 864.16, 863.33, 864, 73/864.01, 864.02, 864.11, 864.13, 73/864.17, 864.24, 864.25
See application file for complete search history.

(56) References Cited

U.S. PATENT DOCUMENTS

| | | | | |
|---|---|---|---|---|
| 5,306,510 | A * | 4/1994 | Meltzer | 422/65 |
| 5,935,859 | A * | 8/1999 | Elliott et al. | 506/33 |
| 6,063,339 | A * | 5/2000 | Tisone et al. | 422/67 |
| 6,203,759 | B1 * | 3/2001 | Pelc et al. | 422/521 |
| 6,232,085 | B1 | 5/2001 | Pantoliano et al. | |
| 6,488,829 | B1 * | 12/2002 | Schroeder et al. | 204/403.01 |
| 6,551,557 | B1 * | 4/2003 | Rose et al. | 422/502 |
| 6,589,791 | B1 * | 7/2003 | LaBudde et al. | 436/55 |
| 6,592,825 | B2 * | 7/2003 | Pelc et al. | 422/521 |
| 6,764,648 | B1 * | 7/2004 | Roach et al. | 422/63 |
| 7,244,396 | B2 * | 7/2007 | Chait et al. | 422/501 |
| 7,790,462 | B2 * | 9/2010 | Fournier et al. | 436/47 |
| 7,858,041 | B2 * | 12/2010 | Muraishi et al. | 422/511 |
| 2001/0014477 | A1 * | 8/2001 | Pelc et al. | 436/49 |
| 2001/0016177 | A1 * | 8/2001 | Pelc et al. | 422/100 |

(Continued)

OTHER PUBLICATIONS

Journal of the Korean Chemical Society, 2005, vol. 49, No. 5, pp. 479-487, "Analyss of the m-value Change in the Equilibrium Unfolding of Hydrophobic Core Variant Ubiquitin", Park, et al.
International Search Report/Written Opinion mailed Apr. 9, 2012 in co-pending PCT application No. PCT/US2011/048799.

*Primary Examiner* — Brian R Gordon
(74) *Attorney, Agent, or Firm* — Nields, Lemack & Frame, LLC

(57) ABSTRACT

A system for automatically creating a denaturation curve is disclosed. In accordance with certain embodiments, a movement system including a unit having a plurality of cannulas is used. The cannulas are in fluid communication with a fluid system, which allows the cannulas to draw in and dispense fluid. A measurement system is included which draws fluid from a well into a detector to determine a characteristic of the fluid. A controller is used to control these systems and also to create a denaturation graph from the measured characteristics. In another embodiment, a plurality of formulations may be created using the system.

17 Claims, 13 Drawing Sheets

(56) References Cited

U.S. PATENT DOCUMENTS

| | | | |
|---|---|---|---|
| 2001/0020588 A1* | 9/2001 | Adourian et al. | 204/451 |
| 2001/0048899 A1* | 12/2001 | Marouiss et al. | 422/100 |
| 2002/0176803 A1* | 11/2002 | Hamel et al. | 422/100 |
| 2003/0062265 A1* | 4/2003 | King et al. | 204/453 |
| 2004/0157266 A1 | 8/2004 | Oas et al. | |
| 2008/0226498 A1* | 9/2008 | Stylli et al. | 422/63 |
| 2009/0298186 A1 | 12/2009 | Brigham-Burke et al. | |

\* cited by examiner

SYSTEM FOR CREATION OF FORMULATIONS AND GENERATION OF DENATURATION GRAPHS

This application claims priority from U.S. Provisional Patent Application Ser. No. 61/375,920, filed Aug. 23, 2010, the disclosure of which are incorporated herein by reference in its entirety.

BACKGROUND OF THE INVENTION

Protein therapeutics is the fastest growing segment of the biotechnology and pharmaceutical industry. Protein therapeutics includes monoclonal antibodies, recombinant proteins, chimeric proteins and other protein receptor constructs. This segment is expected to reach over $70 billion in sales by 2011.

A major hurdle in the development and use of proteins as pharmaceutical drugs is the ability to store, transport and deliver them in a safe stable form. It is well known that factors, such as temperature, solvent, ligands, excipients, pH, and salt concentration, affect a particular protein's stability. The identification of buffer, ligand and excipient conditions that maximize the stability and eliminate protein aggregation is critical during development and often requires the evaluation of hundreds of conditions. This combination of buffer, ligand and excipients conditions is referred to as the storage formulation throughout this disclosure. Unfortunately, it is difficult to vary all of the various parameters to determine the ideal storage formulation for a particular protein.

There are different ways to measure protein stability and each involves disrupting the protein structure through either physical or chemical means. This disruption of the protein structure is referred to as denaturation.

Temperature is one of the most widely used physical denaturants. In this scenario, a protein is subjected to increasing temperature and the corresponding changes in its structure are recorded. One of the disadvantages of temperature denaturation is that proteins typically denature at temperatures at or above 60° C. However, in most instances, the temperatures of interest are physiological (about 37° C.), room (about 25° C.) and storage (4° C.). Thus, results from temperature-based denaturation tests must be extrapolated by more than 25° C. to understand the effects at the temperatures of interest. In addition, most proteins used as biologics undergo irreversible temperature denaturation, which precludes a meaningful calculation of thermodynamic stability at the temperatures of interest. In addition, a formulation that elicits a higher denaturation temperature does not necessarily result in a more stable protein at room temperature.

A second way to measure protein stability is through the use of chemical denaturants, such as urea or guanidine hydrochloride. This method permits measurements to be done at any desired temperature.

The structural stability of a protein is determined by its Gibbs energy of stability, $\Delta G$. This value, $\Delta G$, is a function of temperature, chemical denaturants and other physical and chemical variables. Using the common example of a two state model, where a protein is either folded (i.e. native) or unfolded (i.e. denatured), the protein can transition between these two states:

$$N \Leftrightarrow U,$$

wherein N is the native (folded) state and U is the unfolded state.

Two different rate constants can be defined from this transitional equation. $K_f$ is the rate of the folding reaction; while $K_u$ is the rate of the unfolding reaction. Finally, the equilibrium constant, K, can be defined as the ratio of the unfolding rate to the folding rate, or $$K = \frac{K_u}{K_f}.$$

Furthermore, the Gibbs energy can be expressed in terms of K, as $$\Delta G = -RT \ln(K),$$

where R is the gas constant, T is the temperature, expressed in Kelvin and ln(K) is the natural log of K. Thus, if K is greater than one, the protein unfolds at a higher rate than it folds, and its Gibbs energy is negative. Conversely, if K is less than one, the protein unfolds at a slower rate than it folds, and its Gibbs energy is positive. Also, K is equal to the ratio of the concentration of protein in the unfolded state and the concentration of protein in the folded state K=[U]/[F].

In addition, it has been observed that, for chemical denaturants, a nearly linear relationship exists between the Gibbs energy and the concentration of the denaturant. This relationship may be expressed as $$\Delta G = \Delta G_0 - m^*[\text{denaturant}],$$

where $\Delta G_0$ is the intrinsic Gibbs energy, [denaturant] is the concentration of denaturant, and m is the multiplier, which is unique for a particular protein.

For a native/unfolded equilibrium, the fraction of protein molecules which are unfolded, or denatured, $F_d$, is given by:

$$F_d = \frac{K}{1+K},$$

where K is the equilibrium constant.

This equation can be used to allow calculation of a denaturation curve. When a protein changes from its folded state to an unfolded state, certain measurable characteristics of the protein also change. One such characteristic is the fluorescence of the protein.

While the preferred embodiment described in this application utilizes fluorescence emission (intrinsic or extrinsic) as a way to determine the degree of denaturation or unfolding of a protein, the disclosure is not limited to this technique. There are many physical observable properties and their associated instrumentation, in addition to fluorescence spectroscopy, that are sensitive to the degree of denaturation of a protein. These observable properties include, but are not limited to uv/vis spectroscopy, circular dichroism, nuclear magnetic resonance (NMR), infrared spectroscopy (IR) among others.

FIG. 1 shows a typical urea denaturation curve for an antibody. The y, or vertical, axis is a measure of the intrinsic fluorescence of the protein. The fluorescence of different dyes, usually known as protein probes, can also be used. The horizontal, or x, axis is the concentration of urea in solution with the protein. As can be seen, at a certain point, between 3M and 4M urea, the fluorescence of the protein changes dramatically, indicating that it has denatured.

The generation of the data needed to produce such a graph is laborious. In one scenario, a solution containing the protein and any excipients is prepared. A sample of this solution is then subjected to fluorescent light and the emission is recorded. This is the baseline fluorescence with no chemical denaturant. In some embodiments, an amount of urea is then added to the remainder of the solution, and the light test is repeated on a portion of this modified solution. An additional amount of urea is then added to the remainder of the solution and a third light test is performed. This process is repeated for the number of desired samples. The amount of urea added each time is a function of the desired granularity of the test, and the range of urea molarities to be included. Such a method is prone to errors, as there are cumulative errors due to the constant addition of urea to the remaining solution. In this stepwise urea addition method, the process will result in the dilution of the protein and also a smaller fluorescence signal. In addition, since the solubility of urea is about 10.5M and a final 8M urea concentration is needed, the starting protein solution volume needs to be extremely small. The protein will be significantly diluted as the experiment progresses.

In another embodiment, a plurality of solutions, each with the protein, any excipients, and the proper amount of urea, is individually prepared. Each of these prepared solutions is then light tested to determine its fluorescence. While this method removes the cumulative errors associated with the previous method, it is extremely time consuming, especially for a large number of samples.

The resulting graph, such as that shown in FIG. 1, shows the stability of a particular combination of buffer, ligand and excipient conditions in the presence of a chemical denaturant. More stable combinations have a similarly shaped graph, shifted to the right. Conversely, less stable combinations have a graph shifted to the left. The goal of this testing is to find a combination with the maximum stability in the presence of the chemical denaturant. This combination can then be used as the storage formulation for the protein as it is stored and shipped.

Given the increased importance of developing proteins for pharmaceutical purposes, there is a dearth of systems and methods available to aid in the determination of the ideal storage formulation in which the protein is most stable.

For example, denaturation graphs are an effective way to understand the stability of a protein in a particular buffer solution. However, as described above, the creation of denaturation graphs is tedious and error prone. Furthermore, the testing required to fully understand the effect of changing one or more components of that buffer solution is so labor intensive that it is rarely performed. An apparatus that can be used to create these denaturation graphs would be beneficial.

SUMMARY OF THE INVENTION

A system for automatically creating a denaturation curve is disclosed. In accordance with certain embodiments, a movement system including a unit having a plurality of cannulas is used. The cannulas are in fluid communication with a fluid system, which allows the cannulas to draw in and dispense fluid. A measurement system is included which draws fluid from a well into a detector to determine a characteristic of the fluid. A controller is used to control these systems and also to create a denaturation graph from the measured characteristics. In another embodiment, a plurality of formulations may be created using the system.

DETAILED DESCRIPTION OF THE INVENTION

Figure 1:
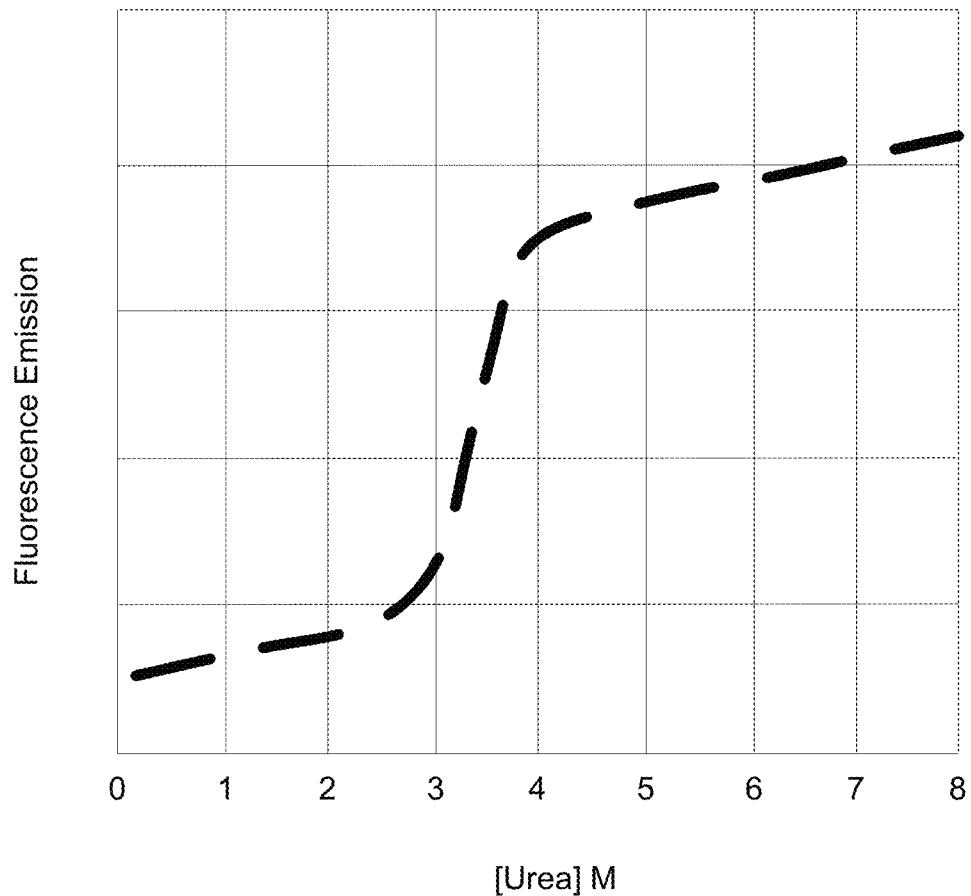
FIG. 1 is a denaturation graph of the prior art.

FIG. 1 shows a typical denaturation graph, used to determine the stability of a protein in the presence of a chemical denaturant, where the chemical denaturant can be urea, guanidinium hydrochloride (GuHCl) or other appropriate chemical. This graph shows the stability of the protein for a particular combination of buffer, ligand and excipients conditions. However, it is often useful to view a plurality of these graphs to understand how changes in the buffer, ligand or excipients affects the stability of the protein.

For example, for a particular combination, it may be of interest to understand how various concentrations of a compound, such as a salt, pH, ligand or other excipient, may affect the stability of the protein. For example, it may be of interest to measure the effects of different concentrations of salt in combination with a particular buffer and ligand. To do this, one may create four different formulations:

Formulation 1: solution with minimum salt and no denaturant
Formulation 2: solution with minimum salt and maximum denaturant
Formulation 3: solution with maximum salt and no denaturant
Formulation 4: solution with maximum salt and maximum denaturant While the descriptions in this disclosure refer to certain formulations having no denaturant, it is understood that, in another embodiment, Formulations 1 and 3 contain a minimum amount of denaturant, which may be greater than 0, while Formulations 2 and 4 contain a maximum amount of denaturant.

To create a denaturation graph, one may begin by using only formulations 1 and 2. By combining these two formulations in different proportions, one can create a plurality of solutions, each with a minimum amount of salt and a varying amount of chemical denaturant. This plurality of solutions can be used to create a first denaturant graph.

Similarly, formulations 3 and 4 can be used to create a second denaturation graph, showing the stability of a solution with a maximum amount of salt with varying amounts of chemical denaturant.

A set of other graphs can also be created, each of which has a salt concentration between the minimum and maximum values. The particular number of graphs within the set is not particularly limited, and can be predetermined or arbitrary. For example, a denaturation graph showing the effect of chemical denaturant, with a salt concentration that is the average of the minimum and maximum values, may be created. In this scenario, a new formulation is created by mixing Formulation 1 and Formulation 3 in equal amounts. This new formulation has a salt concentration exactly halfway between the minimum and maximum values, with no chemical denaturant. Similarly, a second new formulation is created by mixing equal amounts of Formulation 2 and Formulation 4. This new formulation has a salt concentration exactly halfway between the minimum and maximum values, with a maximum amount of chemical denaturant. The denaturant graph for this salt concentration is then created as described above.

Figure 2:
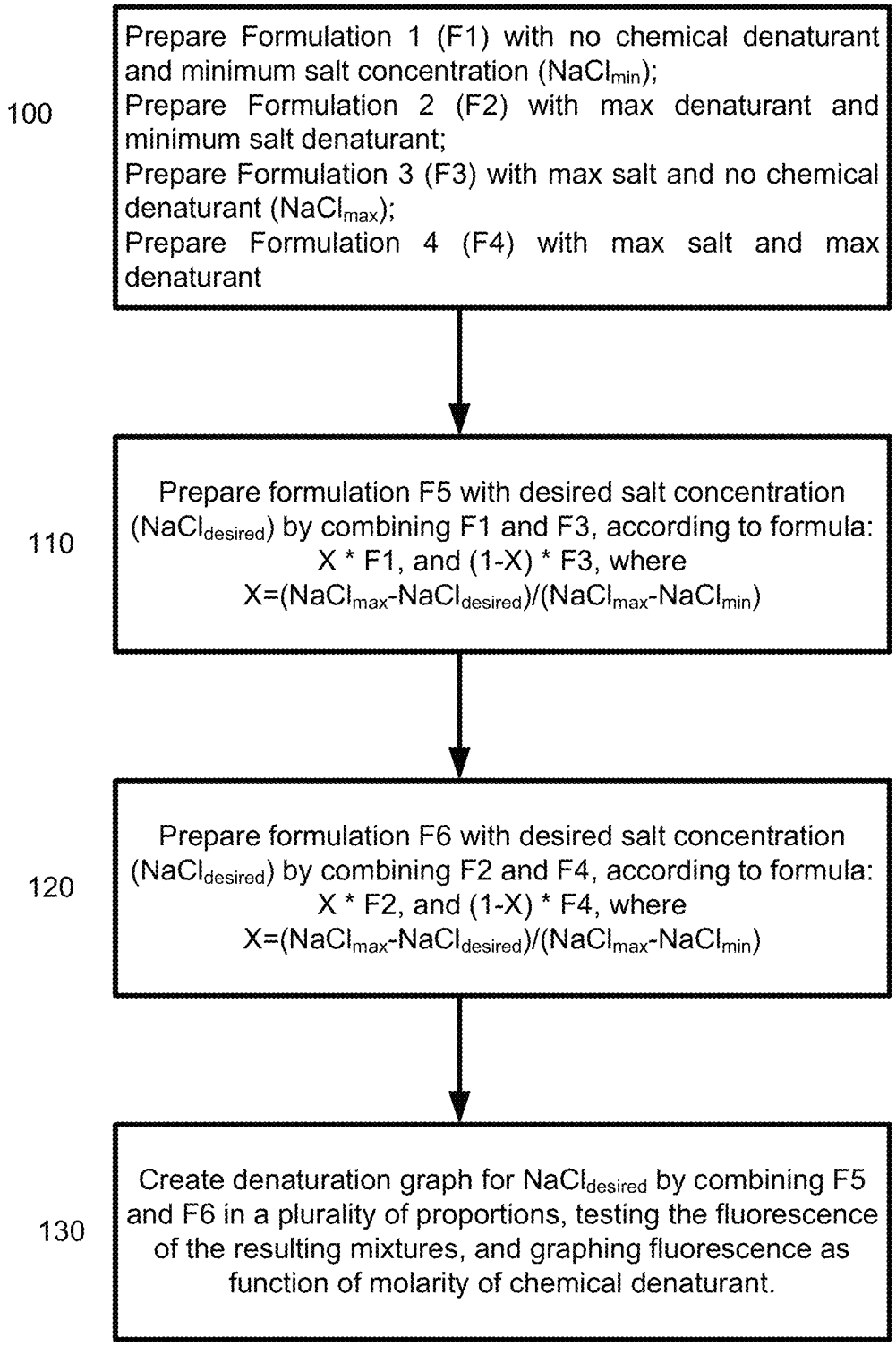
FIG. 2 is a flowchart illustrating a process to generate a denaturation graph with a desired salt concentration.

This process can be repeated a plurality of times to create the required or desired granularity of salt concentration. FIG. 2 shows a flowchart showing this sequence. In step 100, the four formulations, labeled F1 through F4, are prepared. These four formulations represent the four corners of the testing. In step 110, a fifth formulation, which has the desired amount of salt and no chemical denaturant is prepared, using the equation shown. This equation assumes a linear relationship and is used to create any desired concentration between the minimum salt concentration and the maximum salt concentration. Similarly, in step 120, a sixth formulation, which has the desired amount of salt and the maximum amount of chemical denaturant is prepared, using the equation shown. It should be noted that the fifth and sixth concentrations may each be prepared in a separate well or vessel, so as to be available for future use. However, in other embodiments, the fifth and sixth formulations need not be independently created. Rather, the formulations F1, F2, F3 and F4 may be combined in the specific ratios described by these equations in a single well or vessel, without the intermediate formulations F5, F6 being prepared in a separate vessel. Thus, the terms "fifth formulation" and "sixth formulation" are used to express the ratios of F1 and F3, and F2 and F4, respectively, even in the scenario where such formulations may not exist in an isolated vessel. Finally, as shown in step 130, using the fifth and sixth formulations, a denaturation graph can be prepared. For an eleven point graph, the F5 and F6 formulations may be combined as shown in Table 1 below.

TABLE 1

| Point Number | % of F5 | % of F6 |
|---|---|---|
| 1 | 100 | 0 |
| 2 | 90 | 10 |
| 3 | 80 | 20 |
| 4 | 70 | 30 |
| 5 | 60 | 40 |
| 6 | 50 | 50 |
| 7 | 40 | 60 |
| 8 | 30 | 70 |
| 9 | 20 | 80 |
| 10 | 10 | 90 |
| 11 | 0 | 100 |

Each of these points is prepared and then subjected to testing, where the observable property is measured. In one embodiment, this testing includes the measurement of the fluorescence emission of the protein itself (intrinsic) or a fluorescence probe that is sensitive to protein denaturation after being excited with a light of a wavelength that is absorbed by the protein or fluorescence probe. The fluorescence of each data point is measured and recorded. The fluorescence is then plotted as a function of the molarity of the chemical denaturant. The result of this process is a denaturation graph. The process shown in FIG. 2 can be repeated for an arbitrary number of salt concentrations.

Figure 3:
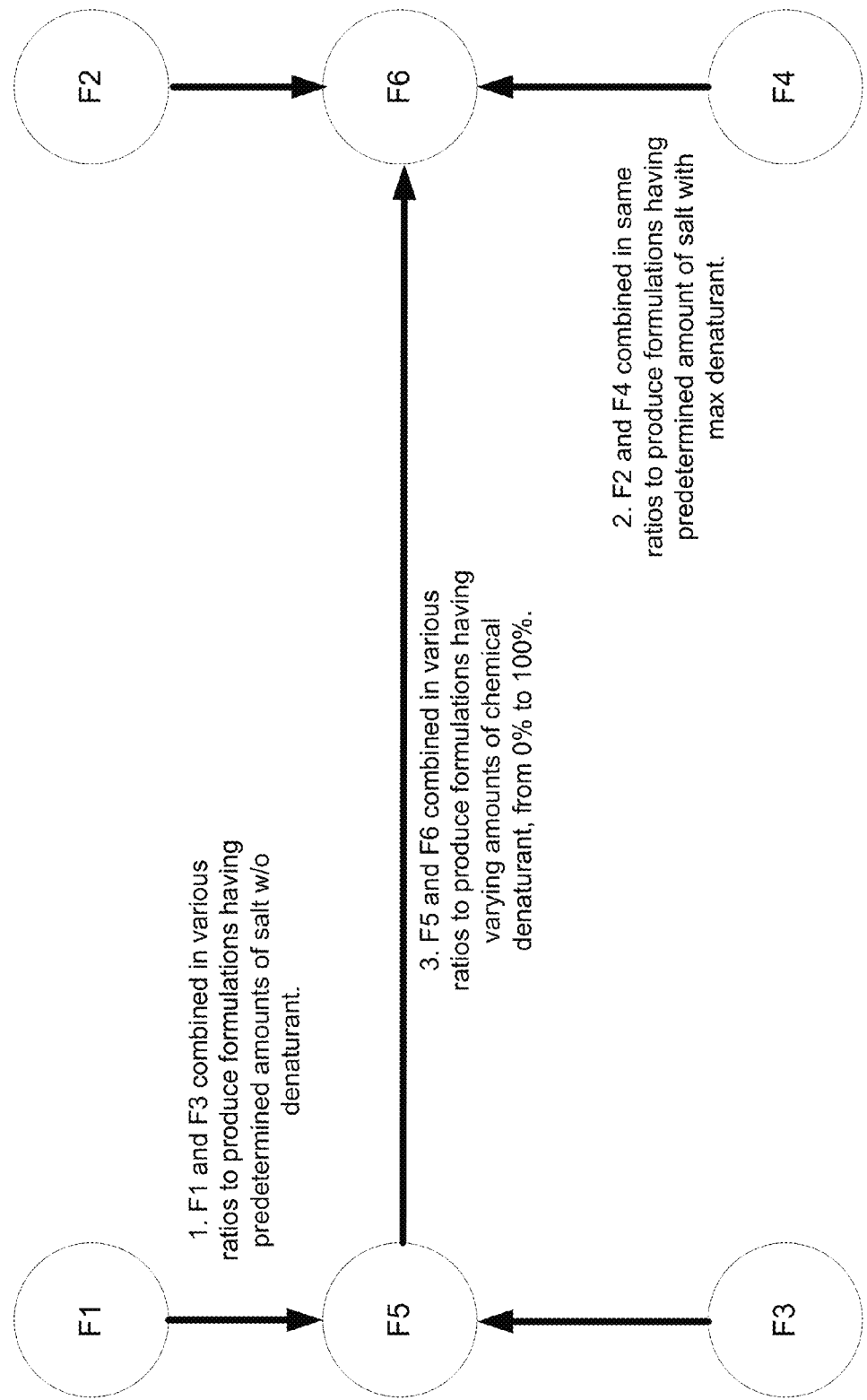
FIG. 3 is a graphical representation of the method of FIG. 2.

FIG. 3 graphically shows how the four concentrations are used to create the plurality of denaturation graphs. Step 1 shows that the two formulations without chemical denaturant F1, F3 are mixed in a predetermined proportion to create a fifth formulation F5. This formulation has a predetermined amount of salt, which is between the salt content in F1 and the salt content in F3. Typically, a linear model is used to determine the value of the salt in F5. For example, assume F1 has 0% salt and F3 has 5% salt. A formulation F5, having 2% salt, is made by combining F1 and F3 in a ratio of 3:2. However, other, non-linear models may be used to determine the content or amount of the variable parameter in the fifth formulation.

Step 2 shows that the two formulations with chemical denaturant F2, F4 are mixed in the same predetermined proportion to create a sixth formulation F6, having the same salt content as F5, but with a chemical denaturant.

Step 3 shows that the fifth formulation may be combined with the sixth formulation in decreasing amounts to create a plurality of formulations having a gradient of chemical denaturants. The fluorescence of each of this plurality of formulations is then measured and a denaturation graph may be created.

Using this method, a plurality of denaturation graphs may be generated, where each represents the effect of an increasing amount of chemical denaturant on a buffer having a specific amount of a variable. The number of different denaturation graphs is not limited by the disclosure. For example, salt in concentrations between 0% and 5% can be tested using steps of varying size. For example, a coarse test may be performed by testing at only 6 different concentrations (0%, 1%, 2%, 3%, 4%, and 5%). In another embodiment, a fine test may be performed by testing the salt concentration at every 0.1% (0%, 0.1% . . . 4.8%, 4.9%, 5.0%). Of course, other step sizes are also within the scope of the disclosure.

In a similar way, the number of points that are tested to make each denaturation graph may be determined by the operator, and may be any arbitrary value. In some embodiments, a 24 point denaturation test is performed. However, other numbers of points, either greater and lesser, may be used.

To create the denaturation curves described above, an automated apparatus may be used. This automated apparatus has at least two different modes of operation. The first mode, known as formulation creation mode, is used to create a plurality of formulations wherein pairs of these formulations each serve as the endpoints for a particular denaturation curve. In this mode, the apparatus can be used to generate a plurality of formulations F5 and F6 which are used to create the intermediate formulations needed for a denaturation curve. The second mode, known as denaturation graph creation mode, the apparatus uses two formulations, to generate a denaturation graph. In this mode, the apparatus can be used to generate one or more denaturation curves, based on starting formulations (such as F5 and F6 as described above).

Referring to FIG. 2, the formulation creation mode is used to prepare one or more sets of formulations (F5 and F6), each having the same composition with the exception being the chemical denaturant. This is shown in steps 110-120 of FIG. 2. The denaturation graph creation mode is used to create a denaturation graph, as shown in step 130 of FIG. 2.

To perform in either of these modes, various components are required. The components of each mode will be described in detailed, followed by a description of how the components perform the required tasks.

The formulation creation mode begins with a number of known formulations. In some embodiments, such as that in FIG. 3, four known formulations are used. These formulations are placed at fixed locations, such that the apparatus is aware of their respective locations. The apparatus includes a controller, which is used to oversee and control the actions of the apparatus. The controller may be a dedicated controller, such as an embedded microprocessor, or may be a general purpose controller, such as a personal computer. In these embodiments, the controller is in communication with a memory element. The memory element may be RAM, DRAM, ROM, Flash ROM, EEROM, magnetic media, or any other medium suitable to hold computer readable data and instructions. The instructions may be those necessary to execute the required methods.

The apparatus uses one or more cannulas, which are used to draw in fluid from a first location and deposit it into at least one second location. In some embodiments, a plurality of cannulas are used. In some embodiments, the cannulas are positioned such that a plurality of cannulas may fit into a single well simultaneously. In other embodiments, the cannulas enter the well sequentially. These cannulas can be used to hold a variety of fluids, including water, a protein, a chemical denaturant, a buffer solution, or other fluids.

The apparatus also has at least one, preferably three actuators, which are used to move the cannulas to various positions within the apparatus. Three actuators allow the cannulas to be moved independently in three dimensions, allowing the cannulas to reach any arbitrary position within the apparatus.

The apparatus also includes at least one pump/syringe system. This pump/syringe system is used to draw fluid from one location or well and deposit it in another location or well.

Figure 4:
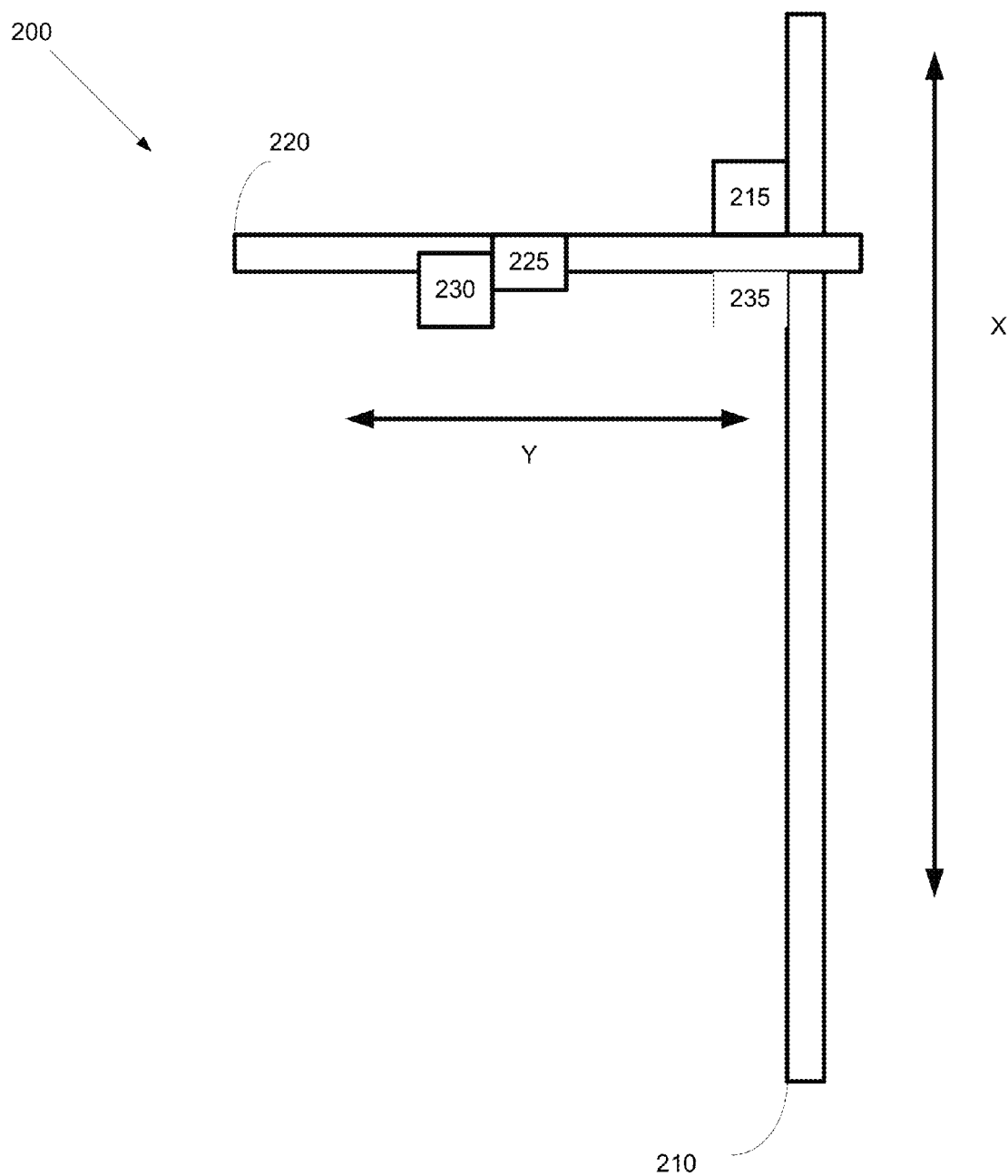
FIG. 4 is a representation of a movement system.

FIG. 4 shows a top view of one embodiment of a motion system 200 used to move the cannulas from one location to another. In this embodiment, a first rail 210 is used to support a second rail 220. A first actuator 215 is used to move the second rail 220 along the path of the first rail 210. A second actuator 225 is used to move the unit 230 carrying the cannulas along the path of the second rail 220. The unit 230 carrying the cannulas preferably has a third actuator (not shown), which allows the cannulas to move in the vertical direction. In some embodiments, a separate actuator is provided for each cannula on unit 230. Thus, actions of actuators 215, 225 can be used to move the cannulas to any position (in two dimensions) within the apparatus. This area within the apparatus may be viewed as a grid, where the first actuator 215 moves along the x axis, and the second actuator 225 moves along the y axis. The third actuator(s) (not shown) allows the cannulas to move in the z direction.

In some embodiments, there may be an actuator 235, which is used to raise either first rail 210 or second rail 220 in the vertical direction. In this embodiment, the cannulas are able to move independently using the actuator(s) on the unit 230, and the entire unit 230 may be vertically translated using the actuator 235.

The controller may be programmed to treat this area as a grid, and the locations of various wells or other locations may be communicated to the controller, such as via an input means, such as a keyboard. Of course, other mechanisms of creating movement in three dimensions are possible and within the scope of the invention.

Figure 5:
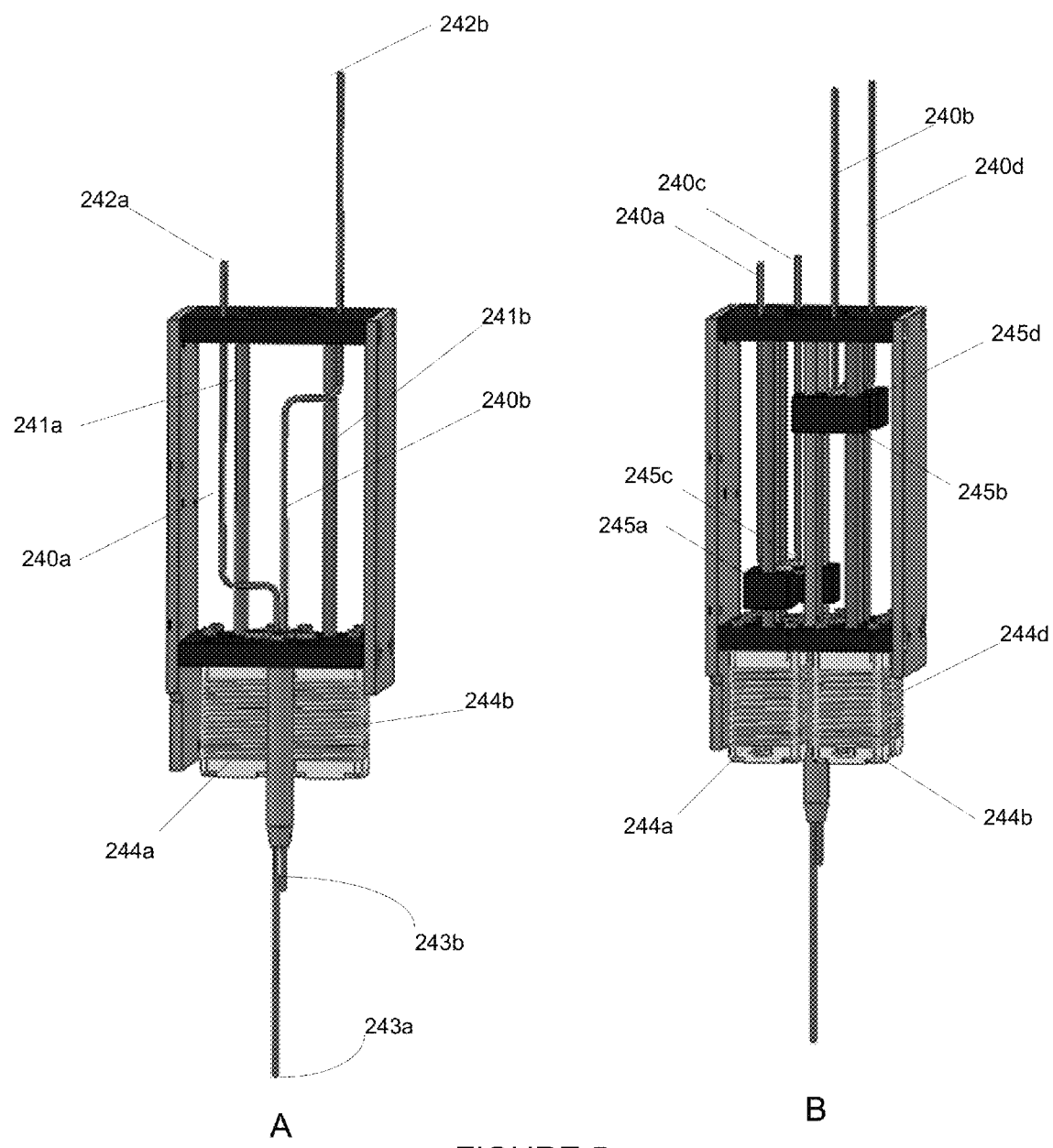
FIGS. 5A-B are representations of a unit having a plurality of cannulas.

FIG. 5A shows a side view of unit 230 used to carry the cannulas 240a-d. In this figure, two cannulas are shown, although the disclosure is not limited to any particular number of cannulas. FIG. 5B shows the unit 230 as it is assembled, allowing the four cannulas to move. In FIG. 5A, a first cannula 240a is shown, with a rail 241a along which the actuator (not shown) moves. Similarly, a second cannula 240b is shown with a second rail 241b. The cannulas 240a, 240b may be shaped such that their distal ends 242a, 242b are shaped apart, while their proximate ends 243a, 243b are very closely spaced so as to allow multiple cannulas to enter a single well simultaneously. FIG. 5B shows four cannulas 240a-240d with the associated actuators 244a-d needed to allow the cannulas to move vertically. In addition, braces 245a-245d are shown which secure the cannulas 240a-d to the rails 241a-d. Each actuator 245a-d is able to translate a respective cannula in the z direction.

Figure 6:
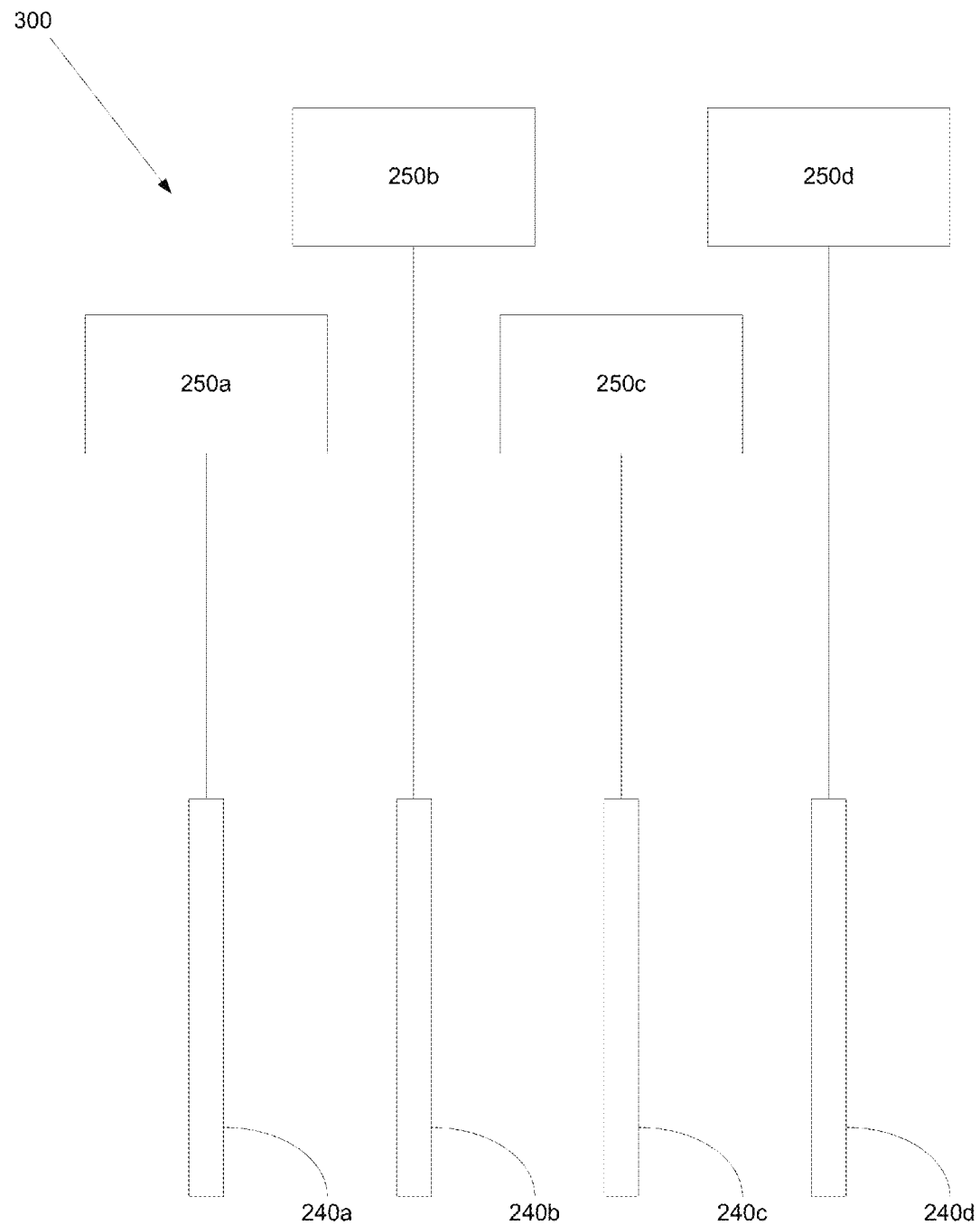
FIG. 6 is a representation of a fluid system according to one embodiment.

In addition to a movement system 200, the apparatus also has a fluid system 300. This fluid system 300 is used to draw fluids into the various cannulas from a first location and dispense those fluids in a second location. In one embodiment, shown in FIG. 6, a separate pump/syringe 250a-d is used with each cannula 240a-d. Thus, when fluid is to be drawn into cannula 240a, the pump/syringe 250a operates to create suction, thereby drawing fluid into the cannula 240a. When the fluid is to be dispensed, the pump/syringe 250a operates in the opposite mode, whereby fluid is pushed out from the cannula 240a.

Figure 7A:
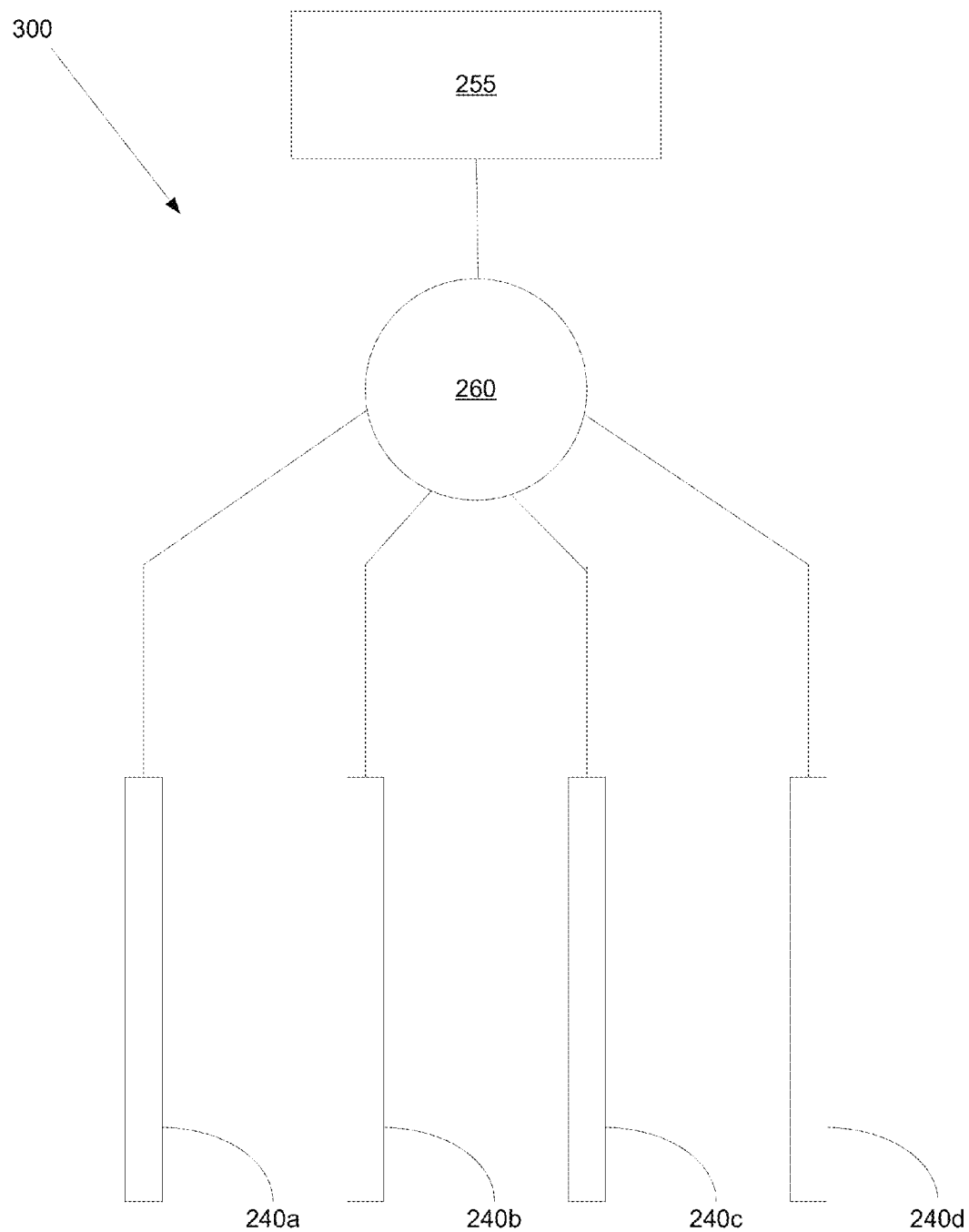
FIG. 7A is a representation of a fluid system according to a second embodiment.

FIG. 7A shows a second embodiment of the fluid system 300, in which a single pump/syringe 255 is used to control all of the cannulas 240a-d. A fluid routing device 260, having a plurality of inputs and a single output may be used. This fluid routing device 260 may be configured so as to connect any one of the inputs from cannulas 240a-d to the output, which is in fluid communication with the pump/syringe 255. Thus, the fluid routing device 260 may be configured to connect the cannula 240a to the pump/syringe 255, so that the pump/syringe 255 may draw fluid into that cannula 240a. The fluid routing device 260 may then be configured to connect the cannula 240b to the pump/syringe 255, so that the pump/syringe 255 may draw fluid into cannula 240b. This configuration may reduce cost by reducing the number of pumps needed for the apparatus.

Figure 8:
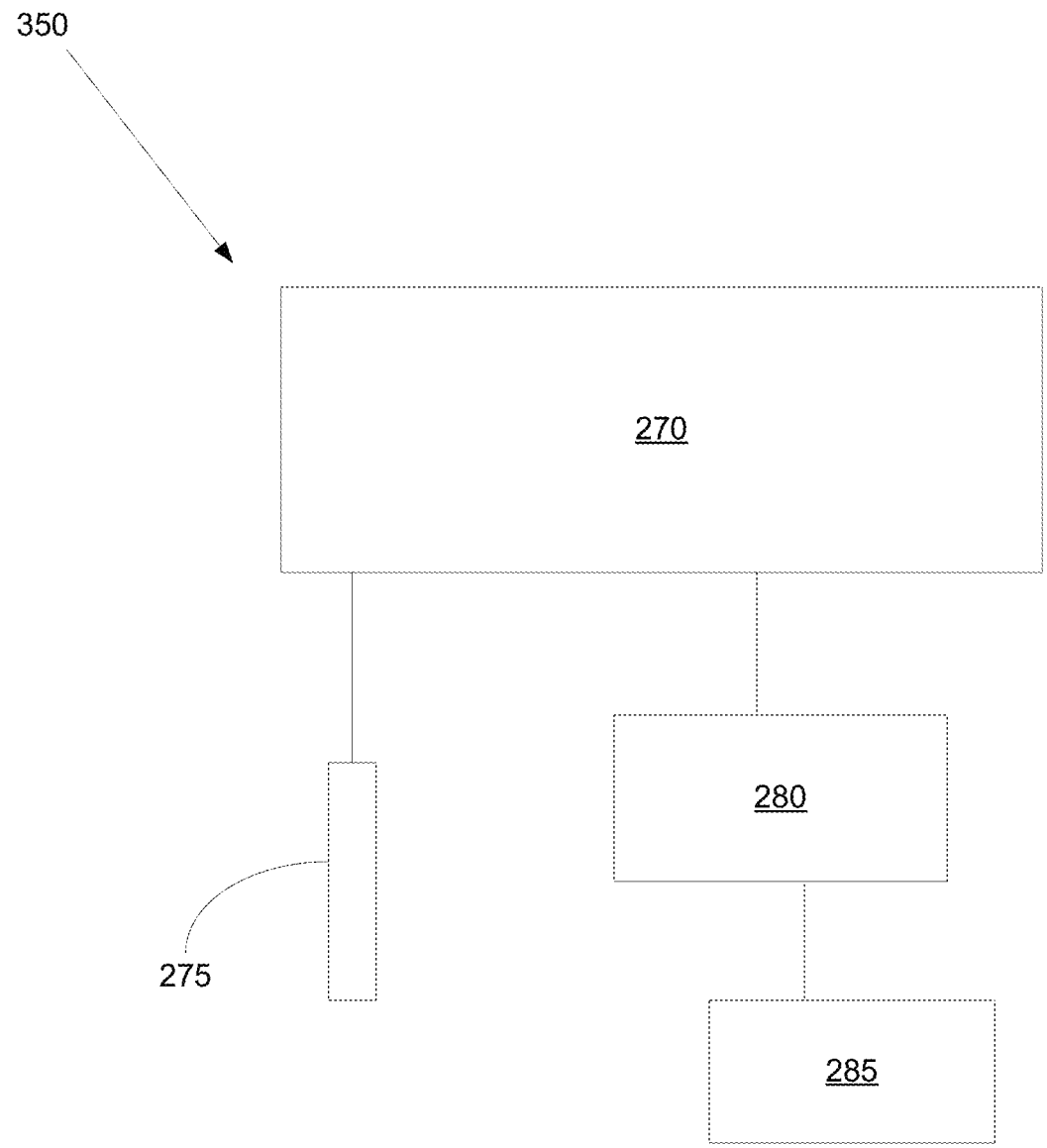
FIG. 8 is a representation of a measurement system.

The apparatus may also include a measurement system 350, where a detector, such as a fluorescence detector, is used to observe and record one or more characteristics of a sample. One embodiment of this measurement system 350 is shown in FIG. 8. In this embodiment, a cannula 275 is used to sip or draw in the sample to be evaluated. A pump/syringe 280 provides the negative pressure needed to draw the sample through the cannula 275 and the detector 270. The detector 270 performs testing on the sample, such as fluorescence testing and records this data. This data may be transmitted digitally, such as via a cable or wirelessly to the controller. The pump/syringe 280 then draws the sample out of the detector 270 and empties it into a waste repository 285. The process can then be repeated by drawing another sample through the cannula 275.

As described above, the apparatus defines a grid within which the movement system 200 can operate. This grid may be used to locate the various wells where fluid may be drawn from or dispensed into. For example, the system may hold one or more multi-well plates. These plates may have 24, 48 or 96 wells. The controller can then either be programmed, or pre-programmed, with the location of these well plates, and the exact coordinates of each well in each plate. Thus, the controller has recognition of each well in the well plates and can move the cannulas to each well, as desired.

Figure 9:
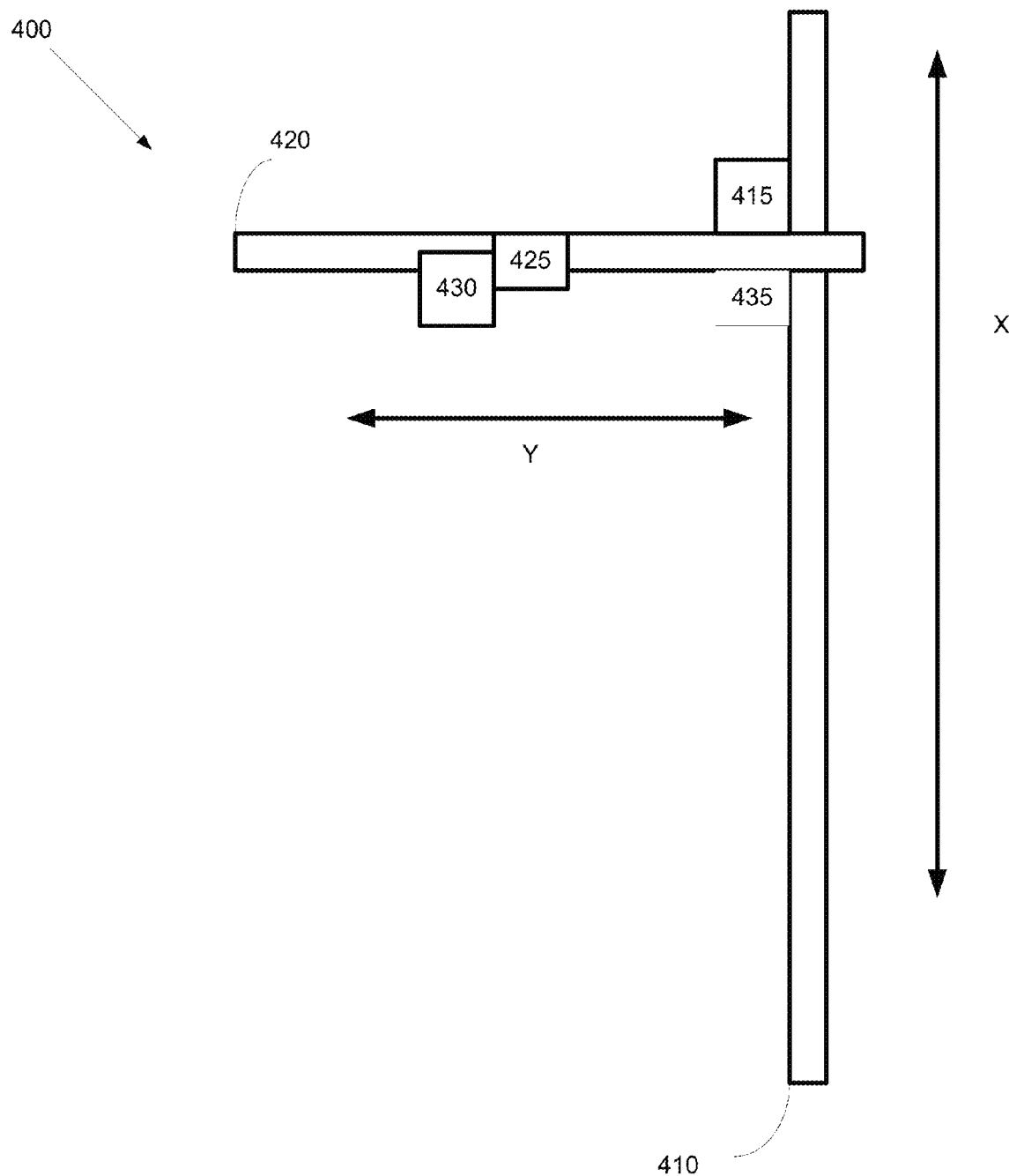
FIG. 9 is a representation of a plate movement system.

In some embodiments, a plate movement system 400 is also included, as shown in FIG. 9. This plate movement system allows the system to move plates to specific places for use, and then to store or otherwise dispose of them. The plate movement system may consist of a second movement system, similar to movement system 200 described above. In this embodiment, a first rail 410 is used to support a second rail 420. A first actuator 415 is used to move the second rail 420 along the path of the first rail 410. A second actuator 425 is used to move the grabber 430 along the path of the second rail 420. The grabber 430 preferably has a third actuator (not shown), which allows the grabber 430 to move in the vertical direction. Thus, actions of actuators 415, 425 can be used to move the grabber 430 to any position (in two dimensions) within the apparatus. This area within the apparatus may be viewed as a grid, where the first actuator 415 moves along the x axis, and the second actuator 425 moves along the y axis. The third actuator 435 is used to raise either first rail 410 or second rail 420 in the vertical direction. Thus, the grabber may be moved, similar to the fashion described above. When it reaches the desired well plate, the grabber 430 may grab the well plate and move it to another location. For example, the apparatus may also contain one or more shelves used to hold these well plates. In some embodiments, these shelves are located in one area of the grid and at various heights. The plate movement system 400 can be used to grab a well plate from a shelf, and move it to a working area of the grid. Following the processing of the well plate, the plate movement system 400 may move the well plate to an area where the measurement system 350 can access it.

Figure 10:
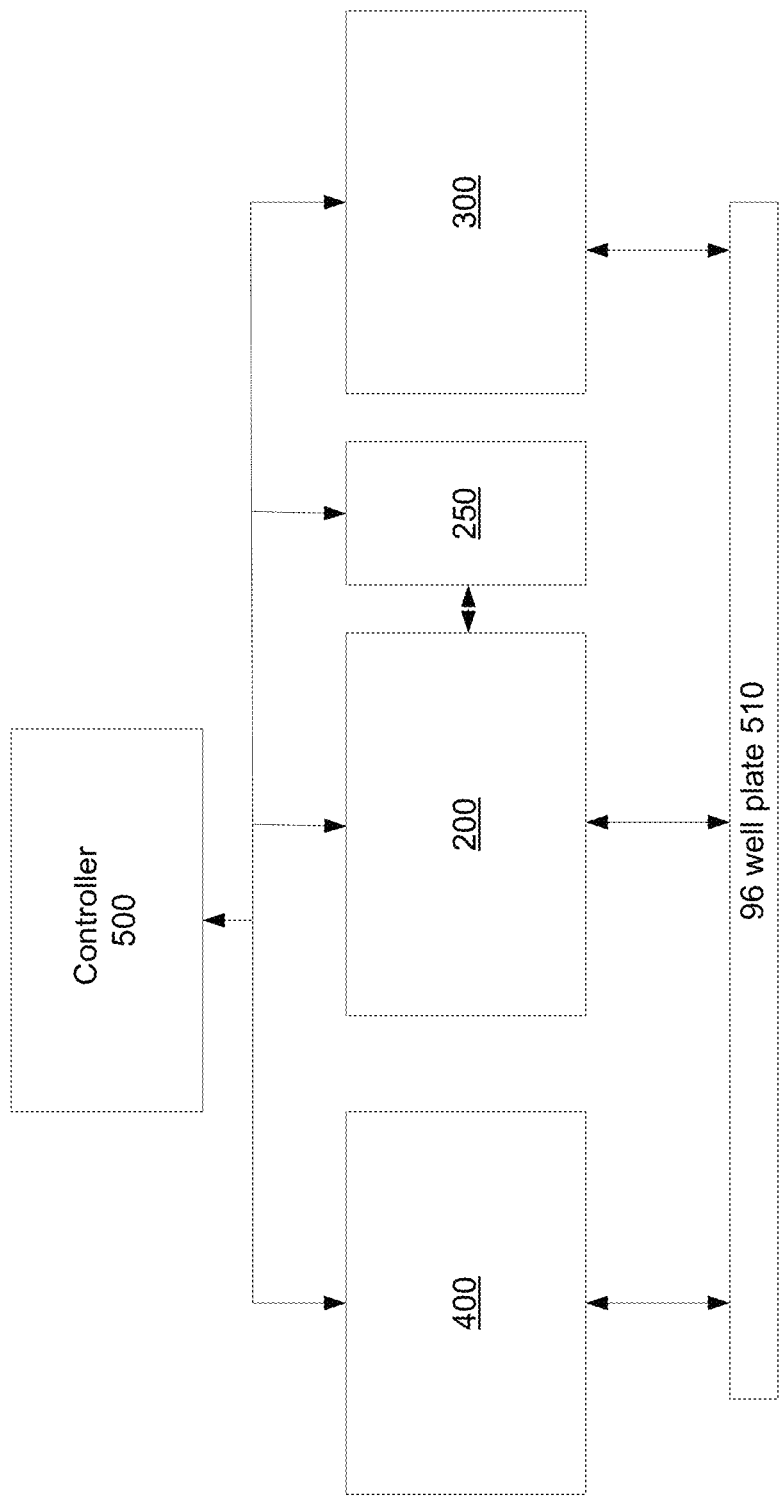
FIG. 10 is a representation of the apparatus.

FIG. 10 shows the interaction of the various components of the apparatus. A controller 500 may be used to control all of the subsystems in the apparatus. Each subsystem may have access to a 96 well plate 510, or other type of fluid receptacle.

Having described the various components of the apparatus, its operation during each of the two modes can be described. One mode, known as denaturation graph generation mode, operates as follows:

Two known formulations, called F5 and F6 are located in two locations within the grid. These locations may be within a 48 or 96 well plate, or may be other fluid holders. In this mode, these formulations were previously created and are not created by the apparatus. In one particular embodiment, twenty four pairs of formulations are prepared and located within a 48 or 96 well plate.

To start the process, the controller 500 instructs the movement system 200 to move the unit 230 with the cannulas over the first well (Formulation F5). The controller 500 instructs the appropriate actuator to lower one of the cannulas 240 into the well to be in a position to draw up a volume of F5. The controller 500 then instructs fluid system 250 to draw fluid into cannula 240a. The controller 500 then instructs the movement system 200 to lift the cannula from the well.

The controller 500 then instructs the movement system 200 to move the unit 230 with the cannulas over a second well (Formulation F6). The controller 500 instructs the appropriate actuator to lower a different one of the cannulas 240 into the well to be in a position to draw up a volume of F6. The controller 500 then instructs fluid system 250 to draw fluid into cannula 240b. The controller 500 then instructs the movement system 200 to lift the cannula from the well.

The controller 500 then instructs the movement system 200 to move the unit 230 with the cannulas over a third well. This third well may be part of a different 48 or 96 well plate. For example, a first 48 or 96 well plate may be used to hold a plurality of pairs of formulations to be tested. A second 48 or 96 well plate is used to hold the various samples that are created from these pairs of formulations. In one embodiment, F5 and F6 are located on a first well plate, while the samples that are to be created based on F5 and F6 are located in a second well plate.

As described above, the controller 500 moves the unit 230 over a third well. This third well plate is also referred to as the first sample well. The controller 500 is programmed with the number of samples that are to be created based on F5 and F6. This number of samples determines the granularity of the resulting denaturation graph. In some embodiments, 12 or 24 samples are created.

At the first sample well, the controller introduces a volume or F5 and no F6. In general, the controller 500 introduced a volume of F5 which is equal to:

$$V_{F5}=(N-n)*V/((N-1)),$$

where V is the total volume to be introduced into each sample well, N is the total number of samples to be created and n is the current sample (i.e. 1 for the first sample, 2 for the second sample, etc.). Similarly, the volume of F6 is equal to:

$$V_{F6}=(n-1)*v/(N-1).$$

In some embodiments, the controller 500 may move the unit 230 to another location, where a third known formulation, such as the protein of interest, is stored. In this embodiment, the protein of interest is drawn into a cannula 240c, and dispensed into each sample well in equal amounts.

After the controller 500 instructs the fluid system 250 to dispense F5 and F6 according to the above equations, the controller 500 may initiate a mixing sequence. In some embodiments, a fourth 240d is used to mix. In this embodiment, all or nearly all of the fluid that was dispensed into a specific well is drawn into the fourth cannula 240d. It is then dispensed back into the sample well. This process may be repeated a plurality of times, which aids in the mixing process.

Each of the sample wells is prepared according to these steps. When all of the sample wells have been prepared, the controller 500 may instruct the movement system 200 to move the unit 230 to a waste repository where all of the fluid remaining in each of the cannulas is dispensed into the waste repository. The system and the cannulas are then ready to repeat this process for generation of the samples for a second or subsequent denaturation graph.

In summary, the four cannulas may be used as follows. The first cannula holds and dispenses F5. The second cannula holds and dispenses F6. The third cannula holds and dispenses the protein. The fourth cannula performs the mixing operation. In other embodiments, three cannulas may be used, where the protein is pre-mixed into formulations F5 and F6.

Figure 7B:
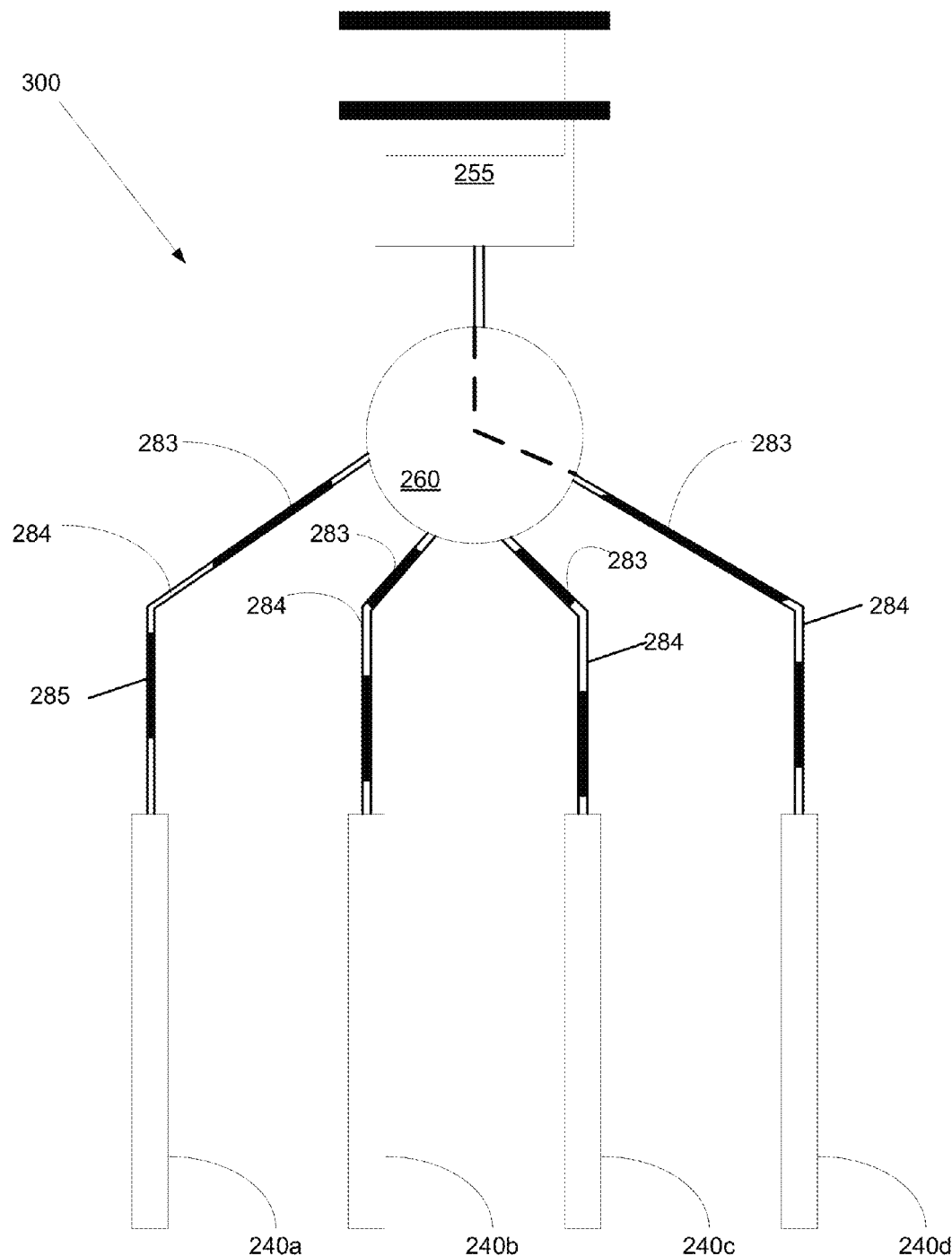
FIG. 7B is a second representation of a fluid system according to the second embodiment.

As described in FIG. 7A, in some embodiments, a single pump/syringe 255 is used. To maintain the integrity of the pump/syringe and all of the cannulas, the following process may be used. Referring to FIG. 7B, first of all, the volume of hose that connects each cannula 240 to the fluid routing device 260 is preferably sufficiently long so as to have a volume greater than that of the fluids being drawn. In some embodiments, the routing device 260 may be a motor driven selector valve. Prior to drawing F5, the first cannula 240a may draw in a volume of water 283, followed by a volume of air 284. After this, the formulation F5 285 is drawn into the cannula 240a. This may be done using a motor driven syringe 255. This process can also be used for the other cannulas 240b-d. This process insures that, should any fluid reach the routing device 260, this fluid is water, and not a formulation. Furthermore, the water, which was drawn into the cannula and hose first, may flush and clean the hose and cannula as the fluid is dispensed into the waste repository.

The process described above uses two formulations (F5 and F6), and optionally a third fluid, such as a protein, and creates a plurality of samples, where each has a specific volumetric ratio of F5 to F6.

After the samples have been prepared, each is then measured using the measuring system 300, described in FIG. 8. In some embodiments, the measuring system has a single cannula 275, which may have a fixed location. In this embodiment, the controller 500 uses the movement system 200 to move the well plate to the cannula 275. For example, the cannula 275 may be downwardly extending. In this embodiment, the movement system 200 moves the well plate such that the first sample well is raised up to the cannula 275. The controller then instructs the cannula 275 to draw the fluid in the first sample well into the detector 270. The detector performs the desired measurement, such as a fluorescence test, and relays the information to the controller, or to a separate computing device. The pump/syringe 280 then draws the sample through to dispenses it into a waste repository 285. The controller 500 then instructs the movement system 200 to move the well plate so that the second sample well is positioned under the cannula 275. The process is then repeated for the second and each subsequent sample well.

Figure 11:
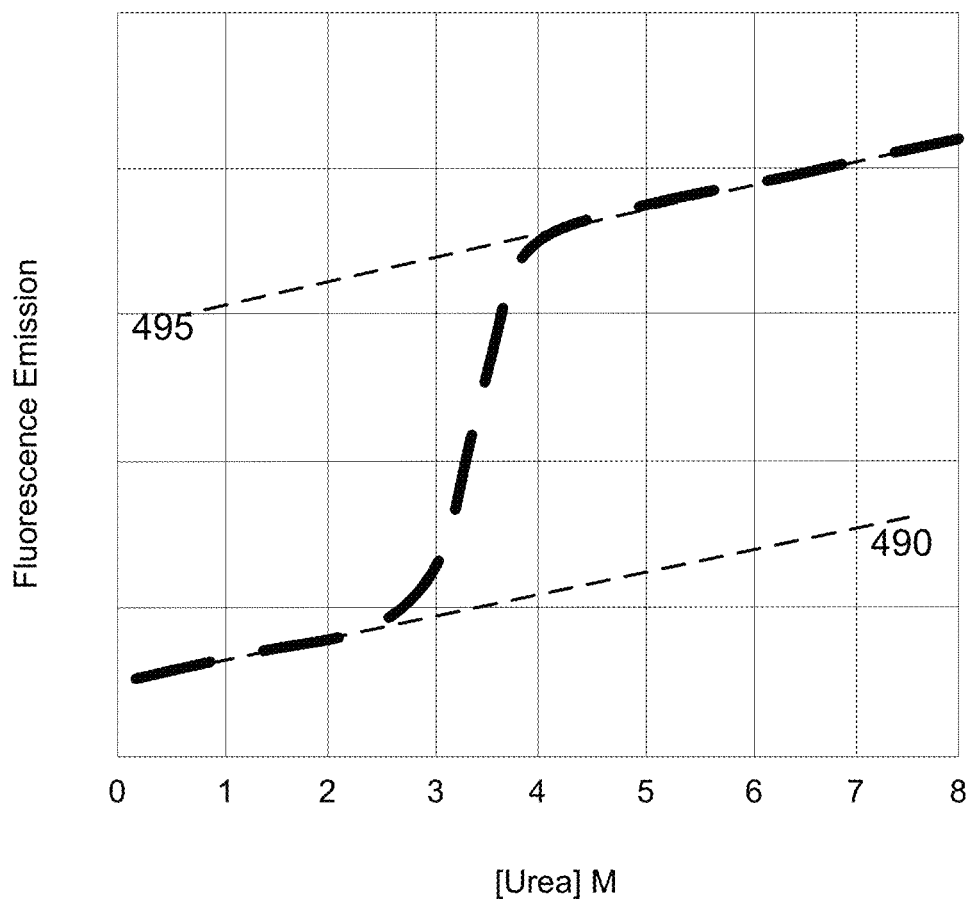
FIG. 11 shows a denaturation graph with best fit lines.

The controller 500 and its associated storage element may also include instructions to create and manipulate denaturation graphs, based on the data received from the fluorescence detector. For example, the controller 500 may select a particular wavelength which is then displayed as a graph of emission versus chemical denaturant concentration, as shown in FIG. 11. The controller 500 may then generate a best fit line 490, which corresponds to the fluorescence emission of native, or folded proteins. The controller 500 may also generate a second best fit line 495, which corresponds to the fluorescence emissions of denatured or unfolded proteins. Using these two lines 490, 495, the controller 500 may generate a second denaturation curve, which maps fraction of protein denatured as a function of chemical denaturant concentration. The value of any point on line 490 may be expressed as f(M), where M is the concentration of chemical denaturant. Similarly, the value of any point on line 495 may be expressed as g(M). Each point P on the denaturation graph can then be expressed as a fraction denatured, according to the equation, (P−f(M))/(g(M)−f(M)).

Figure 12:
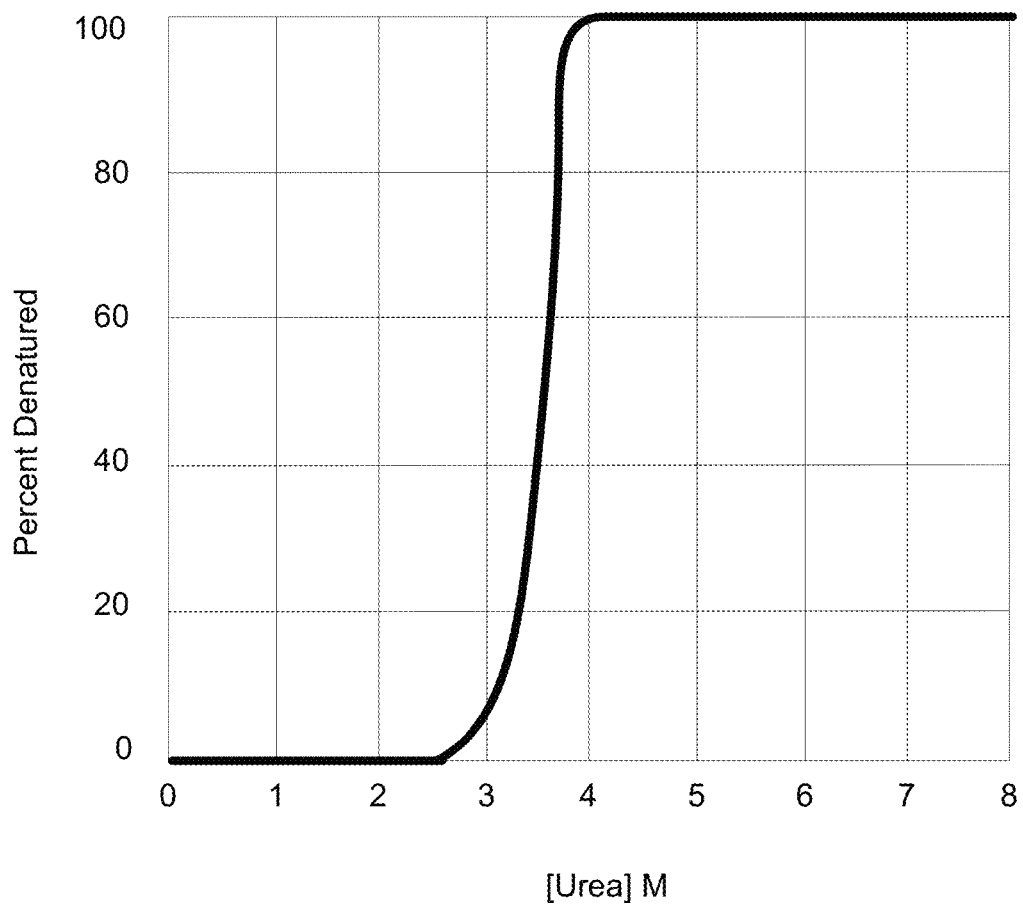
FIG. 12 shows a denaturation graph comparing percent denatured to molarity of chemical denaturant.

These points can then be used to create the denaturation graph shown in FIG. 12.

As noted above, the apparatus also has a second mode, known as formulation creation mode. The apparatus uses many of the system described above in this mode, although the measurement system 350 is not used.

In this mode, a number, preferably four, known formulations are located within the grid of the apparatus. These formulations may be F1-F4, as described in conjunction with FIG. 3. In this mode, the apparatus is used to create a plurality of pairs of formulations (F5 and F6), which serve as the basis for the denaturation graph generation, as described above.

For example, the controller 500 instructs the movement system to move unit 230 to formulation F1, where cannula 240a draws a volume of F1. As described above, a volume of water and air may have been previously drawn to separate the formulations in the fluid system 300. The controller 500 then instructs the movement system to move unit 230 to formulation F3, where a volume of F3 is drawn by cannula 240b.

In one embodiment, the movement system 200 then is moved to a well plate where the first of the F5 formulations is prepared. The volumetric ratio of the F1 formulation to the F3 formulation may be linear. In this case, the equation defined above with respect to F5 and F6 may be used to determine the amount of F1 and F3 that is introduced into each F5 formulation. In other embodiments, a different mathematical relationship is used to determine the amounts of F1 and F3 to be used in each F5 formulation. For example, the controller 500 may be programmed to use a quadratic or cubic equation to determine the amounts of F1 and F3 that should be used in each of the F5 formulations. In some embodiments, a 48 well plate is used to hold 24 pairs of F5 and F6 formulations, where each F5 formulation has a different volumetric ratio of F1 to F3, and each F6 formulation has a corresponding volumetric ratio of F2 to F4. In other embodiments, a 96 well plate is used to hold only F5 formulations, and a second 96 well plate is used to hold only F6 formulations.

Once the first cannula 240a and the second cannula 240b have dispensed F1 and F3, respectively, into a well, a third cannula 240c may be used to mix the formulation, using the process described above. In this embodiment, the fourth cannula 240d is not used in formulation creation mode.

After the different F5 formulations have been created, the apparatus is then used to create the corresponding F6 formulations. The controller 500 may use the movement system 200 to move the unit 230 to a waste repository so that the cannulas may be flushed. The controller 500 then repeats the process of drawing formulation F2 into the first cannula 240a and the formulation F4 into the second cannula 240b, as described above in conjunction with F1 and F3. The controller 500 then prepares the plurality of F6 formulations using the same equations or relationships used to create the F5 formulations.

After this process is complete, one or more pairs of F5 and F6 formulations have been created. In one embodiment, 24 pairs of formulations have been created, which fills a single 48 well plate. In another embodiment, 96 pairs of formulations have been created, where all of the F5 formulations are contained on one 96 well plate, and all of the F6 formulations are contained in a second 96 well plate. In other embodiments, a lesser amount of pairs may be created.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

What is claimed is:

1. An apparatus for generating a denaturation graph from two known solutions, comprising:
    a first known solution;
    a second known solution;
    a multi-well plate comprising a plurality of sample wells;
    a movement system comprising a unit having at least three cannulas, and a plurality of actuators to move said unit to a specific position on a grid,
    at least three vertical actuators disposed on said unit, each to control vertical movement of a respective cannula, wherein said at least three cannulas are positioned on said unit such that all of said at least three cannulas may access a sample well through actuation of said vertical actuators without actuation of said movement system;
    a fluid system in communication with said cannulas, allowing said cannulas to draw in and dispense fluid;
    a measurement system for measuring a characteristic of a sample;
    a controller having a storage element comprising instructions, which when executed:
        actuate said movement system to move said unit to said first known solution;
        actuate said fluid system to draw said first known solution into a first cannula;

actuate said movement system to move said unit to said second known solution;
actuate said fluid system to draw said second known solution into a second cannula;
actuate said movement system to move said unit to a first sample well;
actuate a first vertical actuator, a second vertical actuator and said fluid system to dispense said first known solution and said second known solution into said first sample well according to a predetermined relationship to create a first volumetric ratio of said first and second known solutions;
actuate said movement system to move said unit to a subsequent sample well; and
actuate said first vertical actuator, said second vertical actuator and said fluid system to dispense said first known solution and said second known solution into said second sample well according to said predetermined relationship to create a second volumetric ratio of said first and second known solutions.

2. The apparatus of claim 1, wherein said instructions, when executed, use a third vertical actuator and said fluid system to draw fluid from said first sample well into a third cannula and dispense said drawn fluid back into said first sample well to mix said first and second known solutions.

3. The apparatus of claim 1, further comprising a third known solution, a fourth vertical actuator and a fourth cannula, wherein said instructions, when executed:
actuate said movement system to move said unit to said third solution;
actuate said fluid system to draw in a volume of said third solution into said fourth cannula; and
actuate said fourth vertical actuator and said fluid system to dispense a predetermined volume of said third known solution into said first sample well.

4. The apparatus of claim 1, where said instructions, when executed, use said measurement system to determine a characteristic of a fluid in said first sample well.

5. The apparatus of claim 1, wherein said fluid system comprises a plurality of hoses, each in communication with one of said at least three cannulas in said movement system, a routing device and a pump/syringe, such that said pump/syringe is used to draw and dispense fluid from each of said at least three cannulas.

6. The apparatus of claim 1, wherein said measurement system comprises a detector.

7. The apparatus of claim 1, wherein said plurality of actuators of said movement system move said unit in at least two dimensions.

8. The apparatus of claim 1, wherein said predetermined relationship comprises a linear relationship.

9. The apparatus of claim 1, wherein said predetermined relationship comprises a non-linear relationship.

10. The apparatus of claim 6, wherein said detector comprises a fluorescence detector.

11. The apparatus of claim 3, wherein said third solution comprises a protein, and wherein said instructions, when executed:
repeatedly actuate said movement system to move said unit to each of a plurality of sample wells;
repeatedly actuate said first vertical actuator, said second vertical actuator and said fluid system to dispense said first known solution and said second known solution according to said predetermined relationship to create a plurality of samples, each having a different volumetric ratio of said first and second known solutions;
repeatedly actuate said fourth vertical actuator and said fluid system to dispense a predetermined volume of said third known solution into each of said plurality of sample wells;
actuate said measurement system to determine a characteristic of each of said plurality of samples; and
generate a denaturation graph using said determined characteristics from said plurality of samples.

12. The apparatus of claim 1, wherein said first known solution comprises a first amount of denaturant, and said second solution comprises a second amount of denaturant, greater than said first amount.

13. The apparatus of claim 3, wherein said third solution comprises a protein.

14. The apparatus of claim 11, wherein a time between said dispensing of said third solution and said actuation of said measurement system for a particular sample well is constant for each of said plurality of sample wells.

15. The apparatus of claim 6, wherein said detector detects a characteristic selected from the group consisting of uv/vis spectroscopy, circular dichroism, nuclear magnetic resonance, and infrared spectroscopy.

16. An apparatus for generating a denaturation graph from two known solutions, comprising:
a first known solution comprising a first amount of denaturant;
a second known solution comprising a second amount of denaturant, greater than said first amount;
a multi-well plate comprising a plurality of sample wells;
a third solution comprising a protein;
a movement system comprising a unit having at least three cannulas, and a plurality of actuators to move said unit to a specific position on a grid, at least three vertical actuators disposed on said unit, each to control vertical movement of a respective cannula, wherein said at least three cannulas are positioned on said unit such that all of said at least three cannulas may access a sample well through actuation of said vertical actuators without actuation of said movement system;
a fluid system in communication with said cannulas, allowing said cannulas to draw in and dispense fluid;
a measurement system for measuring a characteristic of a sample;
a controller having a storage element comprising instructions, which when executed:
actuate said movement system to move said unit to said first known solution;
actuate said fluid system to draw said first known solution into a first cannula;
actuate said movement system to move said unit to said second known solution;
actuate said fluid system to draw said second known solution into a second cannula;
actuate said fluid system to drawn said third solution into a third cannula;
actuate said movement system to move said unit to a first sample well;
actuate a first vertical actuator, a second vertical actuator and said fluid system to dispense said first known solution and said second known solution according to a predetermined relationship to create a first volumetric ratio of said first and second known solutions in said first sample well;
actuate a third vertical actuator and said fluid system to dispense a predetermined amount of said third solution in said first sample well;

repeatedly actuate said movement system to move said unit to a subsequent sample well;

repeatedly actuate said first vertical actuator, said second vertical actuator and said fluid system to dispense said first known solution and said second known solution according to said predetermined relationship to create a different volumetric ratio of said first and second known solutions in said subsequent sample well;

repeatedly actuate said third actuator and said fluid system to dispense said predetermined amount of said third solution in said subsequent sample well;

actuate said measurement system to determine a characteristic of each of said plurality of sample wells; and generate a denaturation graph using said determined characteristics from said plurality of samples.

17. The system of claim 16, wherein a time between said dispensing of said predetermined amount of said third solution into a particular sample well and said determination of a characteristic by said measurement system for said particular sample well is constant for all of said plurality of sample wells.

\* \* \* \* \*